United States Patent [19]

Audiau et al.

[11] Patent Number: 5,567,822
[45] Date of Patent: Oct. 22, 1996

[54] PROCESS FOR THE PREPARATION OF 2-AMINO-7-NITROBENZO-THIAZOLES

[75] Inventors: François Audiau, Charenton le Pont; Patrick Jimonet, Villepreux; Serge Mignani, Chatenay Malabry, all of France

[73] Assignee: Rhone-Poulenc Rorer S.A., Antony, France

[21] Appl. No.: 244,390

[22] PCT Filed: Dec. 9, 1992

[86] PCT No.: PCT/FR92/01165

§ 371 Date: Jun. 13, 1994

§ 102(e) Date: Jun. 13, 1994

[87] PCT Pub. No.: WO93/12099

PCT Pub. Date: Jun. 24, 1993

[30] Foreign Application Priority Data

Dec. 13, 1991 [FR] France .................. 91 15486

[51] Int. Cl.$^6$ .................. C07D 277/68; C07D 277/82
[52] U.S. Cl. .................. 548/164; 548/178
[58] Field of Search .................. 548/164, 178

[56] References Cited

U.S. PATENT DOCUMENTS

| | | | |
|---|---|---|---|
| 2,149,051 | 2/1939 | Helberger et al. | 260/158 |
| 3,978,124 | 8/1976 | Fried et al. | 260/558 |
| 4,154,934 | 5/1979 | Bernstein et al. | 546/189 |
| 4,363,913 | 12/1982 | Clark et al. | 548/164 |

FOREIGN PATENT DOCUMENTS 0374041  6/1990  European Pat. Off. .

OTHER PUBLICATIONS

Chem. Abstracts vol. 41, 1947, Abstract No. 754c.
Suzuki et al., Chem. Pharm. Bull. 27(1), 1979, pp. 1–11.
Elguero et al., Bull. Soc. Chem. Belg., 86, n1–2, 1977, 95–96.
Martvon et al., Coll. Czech. Chem. Commun., 39, 1974, 1356–65.
L. E. Fisher et al., Can. J. Chem. 72, 142–145 (1994).
R. T. Morrison et al., *Organic Chemistry* 2nd ed., Allyn and Bacon, Inc., Boston (1969).

*Primary Examiner*—Johann Richter
*Assistant Examiner*—Laura R. Cross
*Attorney, Agent, or Firm*—Finnegan, Henderson, Farabow, Garrett & Dunner, L.L.P.

[57] ABSTRACT

This invention relates to the process for the preparation of 2-amino 7-nitro benzothiazoles of formula (I)

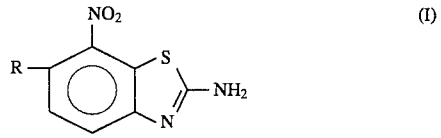

consisting in a) nitrating a derivative of formula (II)

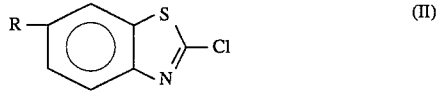

and b) reacting the compound of formula (III)

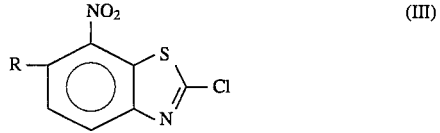

so obtained with caustic ammonia.

10 Claims, No Drawings

PROCESS FOR THE PREPARATION OF 2-AMINO-7-NITROBENZO-THIAZOLES

This application is a 371 of PCT/FR92/ON65 filed Dec. 9, 1992.

FIELD OF THE INVENTION

The present invention relates to a process for the preparation of 2-amino-7-nitrobenzothiazoles of formula:

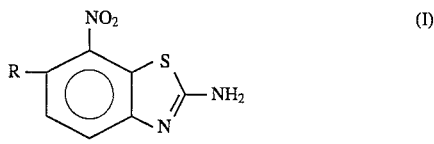

in which R represents an alkyl, alkoxy, alkylthio, polyfluoroalkyl, polyfluoroalkoxy, phenyl, alkenyl, alkylsulphonyl, alkoxycarbonyl, cyano, sulphonamide or dialkylcarbamoyl radical.

BACKGROUND OF THE INVENTION

Direct nitration of 2-aminobenzothiazoles substituted in the 6-position leads to a mixture of 2-amino-4 -nitro- and 2-amino-5-nitrothiazoles (EP 374,041).

It is also known to prepare 4-, 5-, 6- or 7-nitro- 2-aminobenzothiazoles by reacting dinitrochlorobenzenes or dinitrophenyl thiocyanates with thiourea or ammonium thiocyanate (U.S. Pat. No. 4,808,723, R. Hamprech, Chem. Abstr., 101, 211131 and J. Schulze et al., Z. Chem., 20, 436 (1980)); by reacting nitrophenylthioureas with $S_2Cl_2$ or a lead(IV)-phosphate complex (S. Claude et al., Helv. Chim. Acta, 64, 1545 (1981); S. A. Von Mahmoud et al., Prakt. Chemie, 316, 154 (1974)). However, these cyclisations are not always regioselective.

DESCRIPTION OF THE INVENTION

There has now been found, and this forms the subject of the present Application, a process making it possible to obtain industrially the compounds of formula (I) in good yields.

This process consists in a) nitrating a derivative of formula:

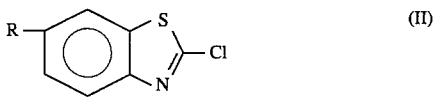

in which R has the same meanings as in formula (I), and b) reacting the compound of formula:

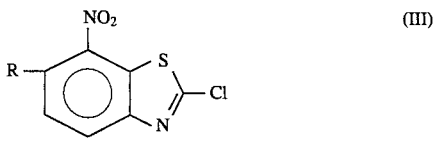

in which R has the same meanings as in formula (I), thus obtained with ammonium hydroxide.

It is particularly advantageous to carry out the nitration of step a) using a nitric acid/sulphuric acid mixture.

Generally, a nitric acid/sulphuric acid mixture containing 1 part by volume of concentrated nitric acid and 1 to 5 parts by weight of concentrated sulphuric acid is used. It is preferred to use a mixture containing 1 part of concentrated nitric acid and 3.7 parts of concentrated sulphuric acid.

The amount of the nitric acid/sulphuric acid mixture is between 1 and 10 parts by volume per part by weight of the derivative of formula (I) used.

The reaction temperature is preferably between 0° C. and 20° C.

Step b) is generally carried out in an inert organic solvent such as an alcohol (methanol or ethanol for example) in a closed reactor.

It is particularly advantageous to perform the process at a temperature between 10° C. and 150° C.

5 to 20 parts by weight of ammonium hydroxide are generally used per part by weight of the derivative of formula (III) used.

The derivatives of formula (III) may be obtained by application or adaptation of the method described in Patent EP 43013.

The compounds of formula (I) may be separated from the reaction mixture according to the usual separation techniques (extraction, chromatography, crystallisation etc.).

The compounds of formula (I) are useful as medicaments or intermediates for preparing medicaments (EP 282,971 and 374,041) or as intermediates for dyes (Patents U.S. Pat. Nos. 2,149,051, 4,363,913, GB 2,163,174).

EXAMPLES

The example which follows shows how the invention may be used.

EXAMPLE 1 a) Preparation of 2-chloro-7-nitro-6-trifluoromethoxybenzothiazole 10 g of 2-chloro-6-trifluoromethoxybenzothiazole are added dropwise over one hour to a mixture, cooled to 10° C., of concentrated sulphuric acid (50 cm³) and concentrated nitric acid (25 cm³). The mixture is then heated for one hour at 60° C. After cooling, the mixture is poured into an ice/water mixture (¼ by weight) and extracted with 3 times 100 cm³ of chloroform. The organic phases are dried over magnesium sulphate and concentrated under vacuum (2.7 kPa). The residue is purified by flash chromatography with a chloroform/cyclohexane mixture (⅘ by volume) as eluent. 6.4 g of 2-chloro-7-nitro-6-trifluoromethoxybenzothiazole are thus obtained, melting at 64° C.

b) Preparation of 2-amino-7-nitro-6-trifluoromethoxybenzothiazole

A mixture of 0.4 g of 2-chloro-7-nitro-6-trifluoromethoxybenzothiazole and 10 cm³ of 33% aqueous ammonium hydroxide solution in 30 cm³ of ethanol is heated at 110° C. in an autoclave for 5 hours. The mixture is cooled and the solvent is evaporated off under reduced pressure (2.7 kPa). After purification by flash chromatography on silica with a cyclohexane/ethyl acetate mixture (⅘ by volume) as eluent, 0.22 g of 2-amino- 7-nitro-6-trifluoromethoxybenzothiazole is obtained, melting at 180° C.

c) Preparation of the intermediates 49.4 g of 2-hydrazino-6-trifluoromethoxybenzothiazole are added over one hour to 97.9 g of thionyl chloride heated to 50° C. The mixture is then heated for one hour at this same temperature and then cooled to 0° C. After addition of 200 g of an ice/water mixture (¼ by weight), the precipitate is filtered off and washed with twice 50 cm³ of water. 54.5 g of 2-chloro-6-trifluoromethoxybenzothiazole are thus obtained, melting at 50° C.

To a suspension of 93.6 g of 2-amino-6-trifluoromethoxybenzothiazole in 420 cm$^3$ of ethylene glycol under a stream of nitrogen are added 48 g of hydrazine hydrate and 42 g of hydrazine dihydrochloride. The mixture is heated for 2 hours at 140° C. After cooling, the precipitate is filtered off and triturated with a water/diethyl ether mixture (¼ by volume). 89.9 g of 2-hydrazino-6-trifluoromethoxybenzothiazole are thus obtained, melting at 208° C.

2-Amino-6-trifluoromethoxybenzothiazole may be prepared according to the method described by L. M. Yagupolskii et al., Zh. Obshch. Khim., 33 (7), 2301 (1963).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Process for the preparation of the compounds of formula:

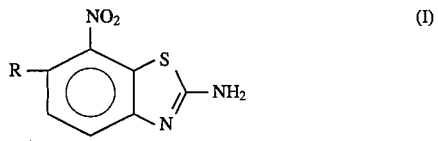 (I)

in which R represents a polyfluoroalkoxy radical, comprising nitrating a) a derivative of formula:

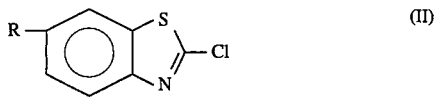 (II)

in which R has the same meanings as in formula (I), and b) reacting compound of formula:

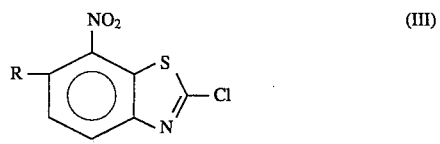 (III)

in which R has the same meanings as in formula (I), thus obtained with ammonium hydroxide.

2. Process according to claim 1, wherein the nitration is carried out using a nitric acid/sulphuric acid mixture.

3. Process according to claim 2, wherein a nitric acid/sulphuric acid mixture is used containing 1 part by volume of concentrated nitric acid and 1 to 5 parts by weight of concentrated sulfuric acid.

4. Process according to claim 2, wherein 1 to 10 parts by volume of nitric acid/sulphuric acid mixture are used per one part by weight of the compound of formula (II) used.

5. Process according to claim 1, wherein the nitration is carried out at a temperature between 0° C. and 20° C.

6. Process according to claim 1, wherein the reaction of step b) is carried out in a closed reactor.

7. Process according to claim 1, wherein the reaction of step b) is carried out in an organic solvent.

8. Process according to claim 1, wherein 5 to 20 parts by weight of ammonium hydroxide are used per one part by weight of a derivative of formula (III).

9. Process according to claim 1, wherein the reaction of step b) is carried out at a temperature between 10° C. and 150° C.

10. Process according to claim 7, wherein the solvent is alcohol.

\* \* \* \* \*